United States Patent [19]
Jones

[11] Patent Number: 5,572,137
[45] Date of Patent: Nov. 5, 1996

[54] PORTABLE DEVICE FOR DETECTING UV LIGHT IONIZABLE GAS OR VAPOR

[75] Inventor: Christopher D. Jones, Salisbury, Great Britain

[73] Assignee: The Secretary of State for Defence in Her Britannic Majesty's Government of the United Kingdom of Great Britain and Northern Ireland, London, United Kingdom

[21] Appl. No.: 182,041

[22] PCT Filed: Jul. 17, 1992

[86] PCT No.: PCT/GB92/01313

§ 371 Date: Jan. 25, 1994

§ 102(e) Date: Jan. 25, 1994

[87] PCT Pub. No.: WO93/02354

PCT Pub. Date: Feb. 4, 1994

[30] Foreign Application Priority Data

Jul. 19, 1991 [GB] United Kingdom .................... 9115659
Jul. 1, 1992 [GB] United Kingdom .................... 9214010

[51] Int. Cl.⁶ .................................................. G01N 27/66
[52] U.S. Cl. .................................. 324/464; 250/382
[58] Field of Search ................................ 324/464, 465, 324/466, 468, 469, 470; 250/423 P, 379, 382, 372

[56] References Cited

U.S. PATENT DOCUMENTS 4,837,440   6/1989   Burtscher et al. .................... 324/464
4,959,010   9/1990   Burtscher et al. .

FOREIGN PATENT DOCUMENTS 0147521   7/1985   European Pat. Off. .
0160888   11/1985  European Pat. Off. .
2208530   6/1974   France .
2656810   11/1979  Germany .
1186525   4/1970   United Kingdom .

Primary Examiner—Walter E. Snow
Attorney, Agent, or Firm—Nixon & Vanderhye P.C.

[57] ABSTRACT

An improved ionizable gas or vapor detector device and method are provided which are capable in preferred forms of sampling $4\times10^{-3}$ cubic meters or more of air $sec^{-1}$ and are responsive to ionizable gas fluctuations at a rate of up to 100Hz. Use of the device of the present invention has proved to provide sensitivity to UV ionizable gas or vapor of over 500 times that of prior devices, giving detection of propylene tracer gas at concentrations of 2 parts per 1,000,000,000 and thus increasing the range from the gas source at which the device may be reliably used. Use for detection of leaks of volatile UV ionizable compounds and for monitoring processes where vapors are emitted is also provided.

23 Claims, 5 Drawing Sheets

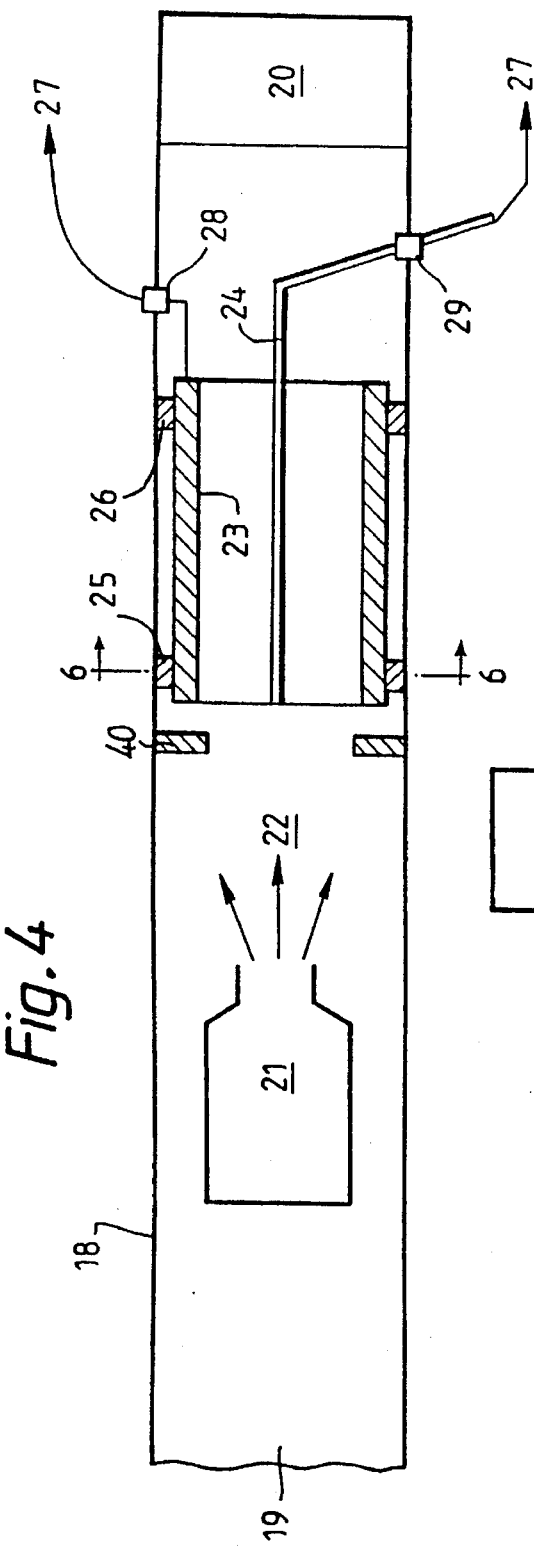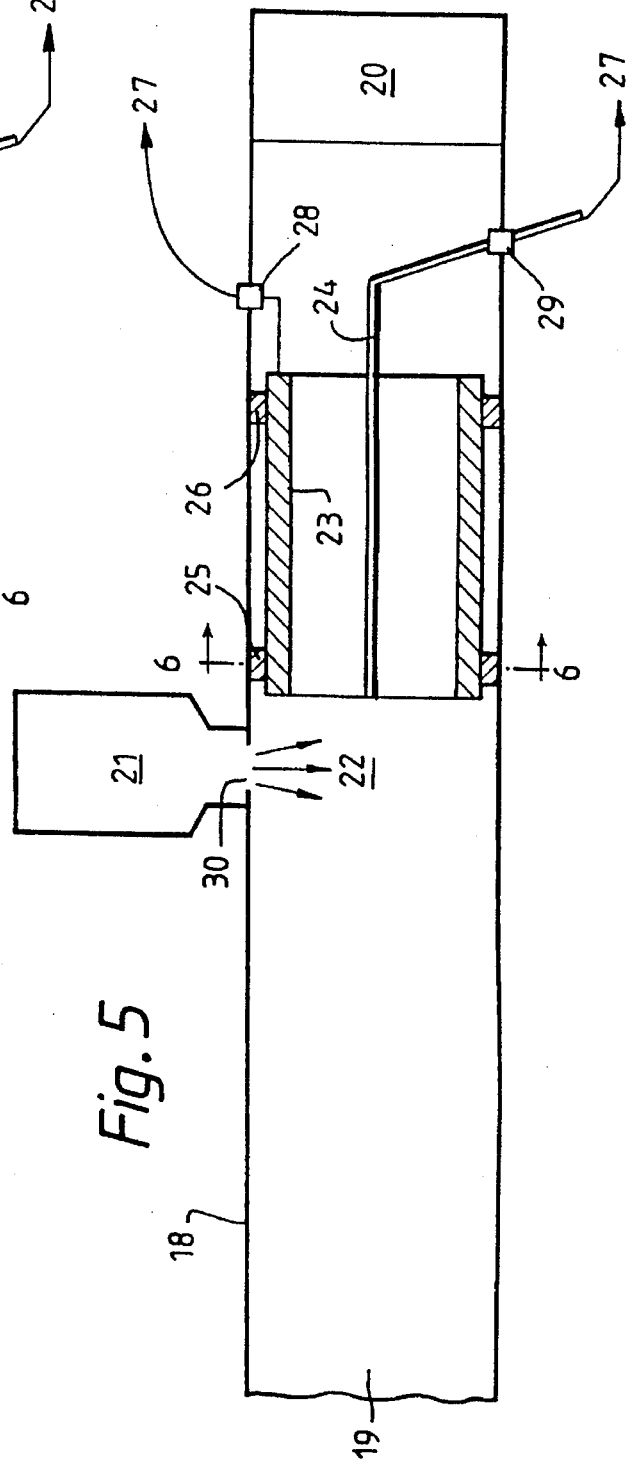

PORTABLE DEVICE FOR DETECTING UV LIGHT IONIZABLE GAS OR VAPOR

BACKGROUND OF THE INVENTION

1. Field of the Invention

The present invention relates to an ultraviolet (UV) light ionisable gas detection device and method of enhanced performance which is suitable for environmental pollution monitoring, atmospheric tracer detection and monitoring gas or vapour emitting processes.

2. Discussion of Prior Art

Ultraviolet light ionisable gas detectors have application in a variety of fields. For example, atmospheric tracer techniques are used for various meteorological and environmental pollution studies where short range diffusion phenomena are under investigation. One known technique involves the release of a tracer compound into the atmosphere and the detection of this at a distant point by use of an ultraviolet light exciter device. In such devices tracer is excited by influence of UV light to produce charged species which are subsequently detected by use of a voltage bias electrode unit.

Typical UV ionisable tracer compounds are olefins, ketones or aldehydes which are capable of taking gas form under standard pressure and temperature conditions, but any volatile or gaseous organic compounds which yield charged materials under influence of ultraviolet light may be used. Typical gaseous examples for tracer use are propylene or butylene.

In a further application of such devices known to the applicant, use of UV light sources of selected wavelength and energy-level makes it is possible to ionise some molecules and not others and thus gives selective detectabililty. For example, comparing the ionisation potential of various compounds, water (12.59 eV), ethane (11.65 eV), ammonia (10.15 eV), nitrobenzene (9.82 eV) and styrene (8.47 eV), it is clearly possible to monitor release of certain compounds against a background of others by selection of UV source wavelength. Such capability clearly has application in a variety of monitoring areas such as in environmental pollution monitoring for release of gases and vapours or monitoring of laboratory processes where gases and vapours are emitted.

One known UV exciter/detector device is described in GB 1576474 and comprises a collector electrode in the form of a washer-like annulus less than 3 mm high and of less than 1 mm material thickness mounted on the gas passage wall and extending across the path of UV radiation emitted from a source behind the electrode. This device has a bias electrode with its distal end central of the annulus and directly exposed to the UV radiation with the collector electrode shielded from the UV radiation by opaque plastics or metallic material.

The collector electrode and bias electrode lie with the major dimensions of their adjacent portions in planes transverse to each other and are adjacent only at the end of the bias electrode. Incoming gas or air for analysis is drawn across the electrode assembly where it is irradiated by UV radiation passing through a window in the shield. This device has a gap between the two electrodes of about 4 mm and the patent specification for this device states that it provides increased sensitivity and linearity over parallel plate electrode devices.

A second known improved UV exciter/detector device also uses a washer like annular electrode upstream of a UV radiation source but in this case an insulator is provided between it and an oppositely chargeable wire mesh electrode. The electrode assembly lies with its major dimension placed directly across the gas flow path and the UV radiation is directed onto the wire mesh electrode such that gas flowing through the system passes directly onto the UV source after passing through the electrode arrangement. This device has a gap of 2 mm between the electrodes.

Whereas the first device has only the bias electrode lying with its major dimension across the flow path, this second device has both electrodes so arranged. In both devices it is desirable to include a dust filter for removing particulates from gases entering as both arrangements are prone to build up of deposits on the UV source and/or electrodes and thus require regular cleaning. Furthermore when used with a olefinic tracer these arrangements are vulnerable to build up of polymers on the surface emitting UV light, this resulting in a polypropylene film where propylene is used.

This second device only operates satisfactorily with an intake air flow of up to $8.33 \times 10^{-6}$ cubic meters $sec^{-1}$ which necessarily limits sensitivity to tracer or other vapour by setting a limit upon the size of sample that can be investigated per unit time. Furthermore the responsiveness of this known device to rapid fluctuation of gas concentration is also limited, typically to about 1 Hz, a feature which is unsatisfactory from a pollution monitoring stand-point or in monitoring fast changing levels of a product or analyte. One particular application for such UV exciter/detector devices has emerged in the field of screening containers for contaminants prior to their reuse. Obviously the ability only to detect fluctuations of 1 Hz renders such screening limited to one container every few seconds if any degree of accuracy is to be ensured. These drawbacks make it desirable to provide a more sensitive and responsive device than that hitherto available.

SUMMARY OF THE INVENTION

The present inventor has provided such an improved device, being capable in its preferred forms of monitoring samples at flow rates of $4 \times 10^{-3}$ cubic meters $sec^{-1}$ or mope and being responsive to detectable gas or vapour fluctuations of up to 20 Hz, or up to 100 Hz in optimal configurations. Use of a device of the present invention has proved to provide sensitivity to tracer of over 500 times that of the prior device, giving detection of propylene gas at concentrations of 2 parts per 1,000,000,000 (US billion: D.p.b.) with accurate measurement of 20 ppb and thus also increasing the range from the analyte or tracer gas source at which the device may be reliably used. It will be realised that such a device may be used to detect leakage of UV ionisable gases down to about 2 p.p.b., and thus is of value in detection in applications other than in tracer studies, eg. in environmental pollution studies and in safety checks at chemical plants or on ships where UV ionisable materials are stored.

In a first aspect the present invention provides a method of detection and/or quantification of an ultraviolet light ionisable gas or vapour in a gas sample comprising the steps of (a) ionising at least a part of any ultraviolet light ionisable gas or vapour present in the sample by irradiating it with ultraviolet light, (b) passing the irradiated sample through a gap between two electrodes units having a voltage applied across them and (c) measuring the current caused by ionised gas or vapour being neutralised by the electrodes and relating that to presence or amount of the ionisable gas or vapour;

characterised in that the ultraviolet light source is positioned relative to the electrodes such that ionisation of the ionisable gas or vapour is substantially completed before the gas enters the gap between the electrodes and that at least a part of the irradiated gas or vapour passes through the gap to reach the outlet.

The electrode units may comprise a single electrode or a group of similarly chargeable electrodes. Preferably the electrode units extend, and thus the gap length extends, substantially in the direction of gas flow for a length at least that at which further increase will not substantially increase ion capture at the voltage used. In a preferred form the method irradiates the sample gas such that at least the negative electrode unit is not directly exposed to ultraviolet light and preferably both electrode units. A further preferred form of the method provides a linear gas flow path for the sample in passage through the irradiation and electrode gap steps.

In a second aspect of the present invention there is provided an ultraviolet light ionisable gas or vapour detector device capable of carrying out the method of the invention.

The ultraviolet light ionisable gas or vapour detector device of the invention comprises a conduit defining a gas flow passage having at least one inlet and at least one outlet; an ultraviolet light source mounted such that in operation ultraviolet light irradiates a portion of the passage; two or more electrodes mounted in a spaced fashion in the passage having coextensive portions facing each other; a voltage supply circuit connected to the electrodes such that at least one might be differently charged to the other or others, current measuring means sensitive to the effects of ions being neutralised upon the electrode surfaces; and a gas flow induction means arranged to draw gas into the at least one inlet, through the irradiated portion of the passage, past the electrodes and out of the at least one outlet; characterised in that the two or more electrodes define a gap between differently chargeable electrode coextensive portions, the gap being substantially downstream of the irradiated portion of the passage such that at least part of the irradiated gas or vapour must pass through it to get to the one or more outlets, wherein the irradiation is not directed onto either of the electrodes from a downstream direction.

The preferred forms of present invention are characterised by having the ultraviolet light irradiated directly into the passage upstream of the electrodes ie. not into the electrode arrangement from a downstream position as in known devices. Furthermore the preferred form of the present invention is such that the major dimension of the electrode arrangement lies with its axis parallel to the conduit axis rather than across it, thus providing a substantially linear flow path in the region of the electrodes at least, preferably through the entire device up to the flow induction means; such path may be curved. While the gas itself flowing through this path is turbid, its turbidity is far less than that produced by the known devices described above. Preferably the coextensive portions and the passage longitudinal axis are substantially parallel to each other.

In operation gas to be analysed is drawn through the passage by the induction means and is irradiated causing ionisable species to be ionised, eg. producing oppositely charged ion pairs or an ion and an electron. The gas then passes into the space between the electrodes. In use the electrodes are differently charged by application of a voltage across them such that ions are attracted to the oppositely charged electrodes. To this end one or more of the electrodes will be collector electrodes for the positively charged ions produced by the UV excitation while the other electrode or electrodes will be conventionally designated the bias electrode or electrodes. Unlike the aforementioned prior art devices the UV light emitted from the source irradiates the conduit upstream of the electrodes but, in preferred devices of the invention, does not substantially irradiate the electrodes themselves or directly irradiate the downstream conduit. The prior devices both direct UV light through an electrode gap from downstream or behind the electrodes relative to the inlet.

The electrode arrangement of the device of the present invention is preferably such that the coextensive portions have a length in the direction of gas flow of at least that equal to their spacing, more preferably with a spacing:coextensive length ratio of 1:1 to 1:25, more preferably of about 1:10 to 1:14. It will be possible to use ratios of less than 1:1 but these will require increased voltages to be applied across them to achieve equivalent results.

Preferably the conduit of the present device is of a tubular form and the passage is provided by the lumen. The tube may take various cross-sectional forms, eg. rectangular, hexagonal, circular or elliptical, but is most conveniently of circular cross-section. Preferred dimensions for the passage diameter in a hand held device are from 1 to 5 cm, preferably about 1 to 2.5 cm. Fixed devices may use wider passages but will need proportionately larger electrodes, voltages and UV sources than hand portable types. Similarly much smaller dimensioned devices are envisaged which might have application in monitoring gases and vapours in individual pipes. The UV light irradiated passage portion is conveniently sited immediately upstream or the electrodes and may suitably be a standard ultraviolet lamp or power and dimensions typical or such detector devices as will be understood by a man skilled in the art (eg. see GB 15764741). HNU and Photovac both produce ranges or suitable lamps for such devices.

The electrode assembly employed by the device of the invention preferably comprises a tubular outer electrode arrangement, more preferably of circular cross-section, concentrically mounted around a parallel, coaxial, inner electrode or electrode unit. Preferably the inner electrode or electrode unit extends substantially the entire length of the outer electrode arrangement and is conveniently a single rod type electrode. The inner diameter of the outer electrode is suitably from 0.6 cm to 4.5 cm with the spacing between it and the outer diameter of the inner electrode being from 0.1 cm to 2.2 cm, preferably between 0.3 cm and 1.6 cm. The electrodes are preferably coextensive over 1 to 10 cm for hand held or stand alone devices such as those used for remote sensing of a given location eg. a point sensor. Such a stand alone sensor may be monitored by telemetry or by examining a record generated thereby. Stand alone devices may of course be connected to a monitoring circuit for remote signalling of the presence or ionisable gas detection and may form part of an extensive system around a given site.

A suitable configuration for a hand held or stand alone device electrode provides an outer/inner electrode spacing of 0.4 cm where the outer electrode arrangement is about 5 cm long and 1 cm in tube inner diameter. The central electrode may be any convenient diameter that provides such a spacing but is conveniently 0.2 cm diameter for this particular arrangement.

The electrode material may be any suitably conductive metal, eg. stainless steel, copper etc and may be advantageously a relatively inert material such as gold plated brass. Insulation of the electrodes from the passage sidewall is provided where this is of non-insulating material. Suitable insulation is provided by use of supports, eg. ring seals or spacers, made of insulating material placed between the outer electrode and the passage wall and by insulating plugs between the connections to the electrodes and the passage wall. Typical insulating materials are polytetra-fluoroethylene (PTFE) and Darvic (ICI RTM). The preferred rod electrode may be suitably supported by an extension of its length which is bent and passes through an insulating plug in the conduit. An alternative arrangement may be provided by two or more projections from the conduit wall to releasably grip an electrode rod, eg. screws insulatedly penetrating the conduit wall, and wherein the electrical connection is provided by a leaf spring conductor.

The outer and inner electrodes may vary in diameter and form along their length and one may extend nearer the UV irradiated zone than the other. Such arrangement need not be static, eg. the inner, central, electrode or electrodes may be movable such as to extend upstream of the outer electrode arrangement or vice versa. Similarly the polarity of the inner and outer electrodes may be reversed without unduly affecting the performance of the device in most circumstances. However, where one electrode is positioned such that UV light may impinge upon it to any degree likely to liberate electrons it is preferred that it is the positive one such that these electrons might be recaptured without increasing background response, ie. noise.

The outer electrode arrangement is preferably of tubular form as described above but may take the form of varying diameter arrangements for both positive and negative electrodes. For example the outer electrode arrangement may take the form of a truncated cone having open ends and sharing substantially the same longitudinal axis as the inner electrode.

The outer electrode may be formed by a single electrode or several similarly chargeable electrodes arranged to substantially form the chosen outer electrode shape. eg. parallel walled tube or truncated cone shape. A single electrode may take the form of a length of wire which may be uncoiled or coiled or may be in the form of a wire grid. particularly if it is the outer tubular electrode arrangement. A truncated cone electrode may be configured with either its larger or smaller open end toward the upstream part of the conduit but if employed will preferably present the larger opening upstream. It is envisaged that the simple coaxial 'Gerdien' tube arrangement having constant diameter of inner and outer electrodes will suffice for most uses.

The electrodes are suitably biased by setting up a DC voltage of between 100 and 1000 volts, more conveniently 100 and 500 volts, across them by use of a circuit comprising a power source, typically being a battery or solid state invertor. Other sources will occur to a man skilled in the art. The voltage should be selected such that the device operates in the saturation region, ie. such that further increase in voltage will not result in increased collection of ions. Measurement of the amount of ionised gas may be derived by use of a sensor circuit eg. including an ammeter or some other such current indicating device in the power circuit. A typical hand held device as described above is capable of detecting 2 p.p.b. and can operate on a 12 volt supply producing 300 volts EHT when other convenient parameters are used, but other suitable voltages will be determinable by the skilled man.

If lower voltages or higher throughput of air is desired then the length of the electrodes should be increased or their spacing decreased if sensitivity is to be maintained. Extending the area over which ultraviolet light is contacted with the gas will also help optimise the sensitivity of the device at higher throughputs without the need to increase UV energy levels to those at which oxygen becomes charged but it should be noted that frequency responsiveness may fall. The sensitivity of the optimised device, eg. using a UV source ionising at less than 12.59 eV, is such that water vapour levels found in human breath will not affect the electrode current while pollutant or tracer detection is sensitive (eg. at 2 p.p.b. propylene).

By use of electrode configurations of the present invention it is possible to operate without a dust filter without undue, ie. significant, build up upon the electrode surfaces. Use of electrode spacings 0.4 cm and above further improves reliability in this respect while the combination greatly enhances throughput capability.

A further preferred refinement of the present device employs the use of an increased Mount of metal in the construction of the passage with the effect of reducing absorption/adsorption of tracer materials upstream of the UV source and electrodes with attendant decrease in slow release of tracer which obscures later readings. Conveniently therefore items such as the passage walls are fabricated from a metal of relatively high electrical resistance and more preferably of reasonably high work function with regard to emission of electrons on irradiation with UV, and which does not retain traces of target gas upon its surfaces; such metal always being insulated from the electrodes. Aluminium is an example of a readily available metal meeting these requirements and stainless steel may be used; the electrode must be insulated from the conduit in each case. However, it will be realised that non-metal construction of non-electrode components is also applicable to the present devices, particularly where a corrosive environment is being monitored.

A preferred embodiment of the present invention provides a device having the ultraviolet light source mounted upstream of the electrodes. Thus the UV source may be provided such that it emits light toward or away from the electrodes from a position within the conduit upstream of them. Where the light is emitted toward the electrodes then at least the more negative electrode or electrodes may be shielded to maintain sensitivity. Most preferably however the UV light source is mounted to the side of the conduit such that it emits UV light substantially transverse to the conduit. In this way air/gas flow is not impinged directly onto the UV source and does not result in problems caused by deposit build-up where the calibration and discrimination of the device may be upset due to weakening UV power, ie. flux.

The side mounting of the UV source may be such that the UV emitting surface forms part of the conduit wall or may be such that light is emitted from outside the conduit and enters through an aperture or UV transparent window. It will be realised that more than one UV lamp may be provided such that they irradiate the interior of the conduit through apertures or windows radially spaced around the conduit periphery at a set distance upstream from the electrodes; in this way an increased amount of target gas molecules may be ionised and thus sensitivity increased. It will be realised that UV light has a relatively short penetration through air and thus such arrangements will allow more effective irradiation of conduits of diameter greater than the effective ionising range of the UV source. In a further arrangement an annular UV lamp may be used to irradiate the conduit over any angle up to 360 degrees around the gas flow path, such lamp forming part of the conduit wall if necessary.

The UV source may be AC or DC driven, the latter allowing simplified circuitry as the need for an AC generator eg. radio frequency generator, is dispensed with when operating from a DC source such as a battery or solid state invertor.

In one embodiment several such apertures or windows are provided or a continuous aperture or window extends longitudinally along the conduit wall such that the distance between the ultraviolet light ionisation and the detection step at the electrodes is variable to alter the sensitivity to ionized species of different ionisation duration ie. recombination rates. In a particular embodiment the conduit is moveable along its longitudinal axis to align selected apertures with the UV source and thus provide a variance in the distance between it an the electrodes. Most preferably the UV source will be easily accessible for interchanging UV sources of different wavelengths or for replacement purposes, eg. for when detection of different compound is intended, when sensitivity has deteriorated due to use to detect propylene gas over a long period or on lamp exhaustion.

By use of sources, eg. lamps, of different wavelength emission in the same device, whereby wavelength may be altered by the operator by eg. a turn of a switch, it will be possible to confirm the presence of a gas of a specific band of ionisation energy. For example, to indicate presence of hydrogen sulphide (10.46 eV) in the presence of styrene (8.47 eV) the operator can first irradiate with a source of higher energy, then with one of energy insufficient to ionise the hydrogen sulphide, and use the difference in current to determine the type of compounds in the gas detected. Thus a device with two or more different UV wavelength lamps may be used to advantageous effect.

The UV irradiated zone should preferably be as close to the electrodes as possible while avoiding significant ionisation of material in the space between them. While the possibility of some UV light impinging upon some of the electrode material is envisaged and its effects may be countered as previously described, this preferably should be kept to a minimum or avoided altogether. If very high flow rates are to be used it will be possible to have the irradiation zone further upstream but this will be a matter for determination by the person skilled in the art dependent upon the intended use of the device.

The gas flow induction means, or aspirator, is conveniently in the form of an electric fan. Flow rates of $4 \times 10^{-4}$ cubic meters $sec^{-1}$ may be conveniently achieved using a radial ran, but for increased flow rates eg up to $4 \times 10^{-3}$ cubic meters or more $sec^{-1}$, a centrifugal fan may conveniently be used.

It will be realised by those skilled in the art that the device of the present invention may be manually set with regard to operation of its electrode, pump (aspirator) and UV component operation. It will also be realised that, in common with existing UV detector devices, the device may conveniently be automated, eg. with computerised or microchip control, in order that rapid set up is possible for given requirements or that a multiwavelength device reading may be rapidly interpreted.

BRIEF DESCRIPTION OF THE DRAWINGS

The present invention will now be illustrated by way of example only, by reference to FIGS. 3 to 8 and their associated description, and the prior art devices shown in FIGS. 1 and 2; other embodiments of the invention will occur to the man skilled in the art in the light of these.

FIG. 4 shows a diagrammatic cross section through an elevation of a tubular conduit of a device of the present invention wherein the UV source is positioned in the conduit upstream of the electrodes.

FIG. 5 shows a diagrammatic cross section through an elevation of a tubular conduit of a preferred device of the present invention wherein the UV source illuminates the upstream portion of the conduit from the outside via an aperture in the conduit wall.

DETAILED DISCUSSION OF PREFERRED EMBODIMENTS

Figure 1:
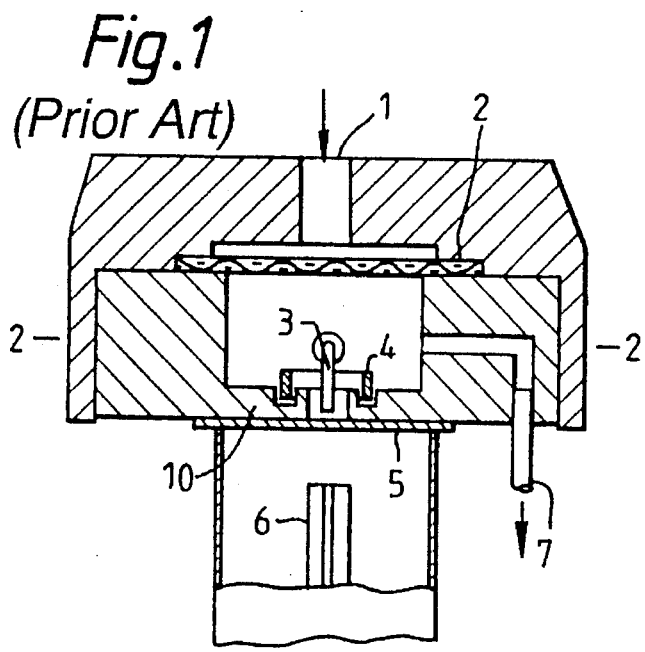
FIG. 1 shows a diagrammatic cross section through an elevation of the prior art detector device of GB 1576474.

The prior art device shown in FIG. 1 comprises an inlet (1) for sampled gas, such as air containing contaminants, having a dust filter (2) allowing passage of gas. Air flows in the direction of the arrows under influence of flow induced by a pump (not shown) connected to a conduit (7). Downstream of the filter (2) is an electrode chamber containing a pair of electrodes (3) and (4); electrode (3) being biased to +180 V or +300 V depending upon application. Ultraviolet light is irradiated from a collimated source (6) through a magnesium fluoride window (5) and onto the electrode assembly; electrode (4) being protected by shield (10).

Figure 2:
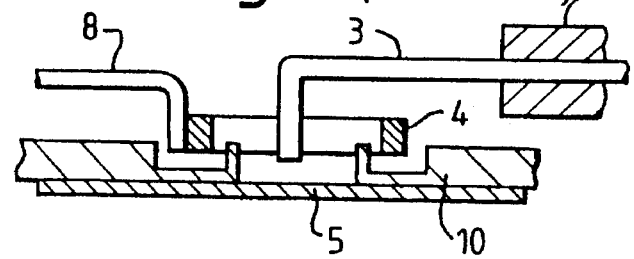
FIG. 2 shows a diagrammatic cross section through the electrode arrangement of FIG. 1 as viewed from 2 to 2.

The electrode assembly of this device is shown as view from point A' to point A in FIG. 2. The electrode (4) is supported on a connector (8) while electrode (3) is supported by insulator (9).

Figure 3:
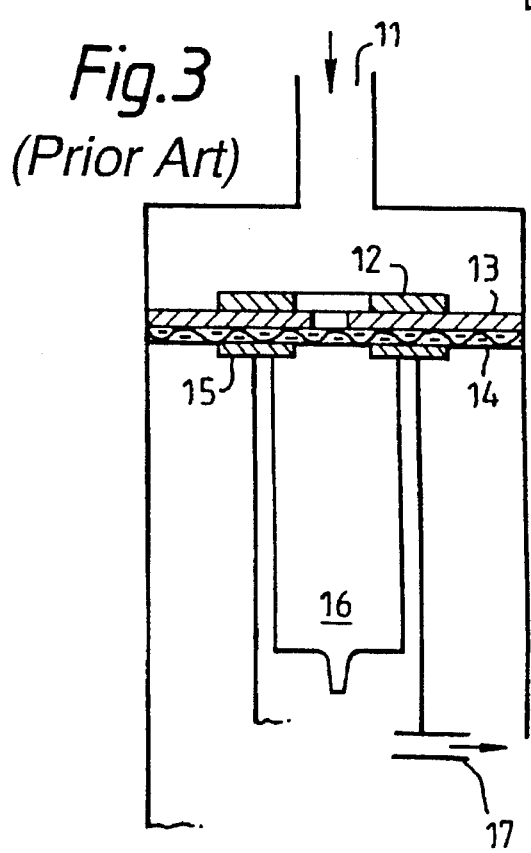
FIG. 3 shows a diagrammatic cross section through an elevation of the second prior art device described above.

The second prior art device described above is shown in cross section in FIG. 3. Sampled gas enters through inlet (11) and exits through conduit (17) under influence of a pump (not shown). The gas passes through a central passage in a first electrode (12), through a hole in an insulator (13) and then through a conductive wire mesh connected to a second electrode (15). UV irradiation is provided by a UV source (16) and directed at the electrode arrangement from the downstream side of the electrode assembly.

A device of the present invention is shown in FIG. 4 and comprises an aluminium or stainless steel tube (18) of approximately 2.5 cm diameter having an open inlet (19) at one end and a fan unit (20) at its opposed outlet end such that in operation it draws air through the inlet and along the length of the tube. An ultraviolet lamp (21) is mounted within the tube passage such that in operation ultraviolet light is directed (see arrows) downstream into an exciter zone (22). Downstream of the exciter zone is provided a coaxial electrode unit comprising a tubular outer electrode (23) with a rod inner electrode (24) positioned so as to extend along its longitudinal axis.

The electrode (23) is mounted upon insulating rings (25) (26) such that its wall is coaxial with that of the tube (18) and is connected to one leg of a DC electrical power supply circuit (27) (not shown) by a wire passing through an insulating plug (28) in the tube wall. The main body of the electrode (24) lies with its longitudinal axis along the longitudinal axis of both the tube (18) and outer electrode (23) and is connected to the other leg of the power supply circuit (27) by a portion that is bent such that it projects, through an insulating plug (29), through the tube wall. In this arrangement of the present invention an annular plastics shield (40) protects the outer electrode from direct irradiation with UV light.

Figure 6:
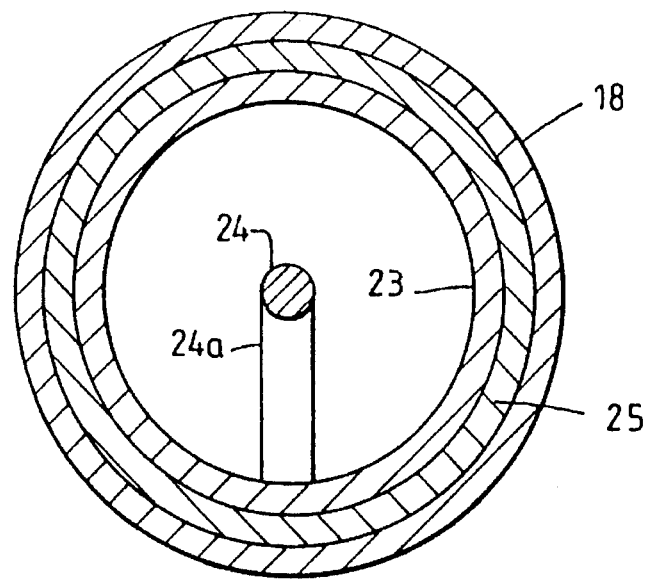
FIG. 6 shows a diagrammatic cross section through line 6—6 of the electrode unit of the conduit of FIGS. 4 and 5 of enlarged scale.

The electrodes are both made of gold plated brass, the plugs (28)(29) are made of polytetrafluoroethylene and the rings (25)(26) are made of Darvic (ICI RTM). The rings are mounted such as to prevent air flow around the outside of the outer electrode between it and the tube inner wall as is best illustrated in FIG. 6. The power supply circuit also includes the current measuring device and may be connected to a set threshold alarm circuit ie. activated above a selectable level of current, to a chart recorder for later analysis of readings, or to a telemetry device.

A preferred device of the present invention is illustrated in FIG. 5 and comprises an aluminium or stainless steel tube (18) of approximately 1 cm diameter having an open inlet (11) at one end and a centrifugal pump (a centrifugal fan) (20) at its opposed outlet end such that in operation it draws air through the inlet and along the length of the tube. On an upper side of the tube is mounted an ultraviolet lamp (21) such that in operation ultraviolet light is directed (see arrows) into the tube interior in an exciter zone (22) through an aperture (30) in the tube wall. Downstream of the exciter zone is provided a coaxial electrode unit arrangement as described above for FIG. 4.

FIG. 6 shows a cross section at point A–A' of the electrode unit of the devices of FIG. 4 and 5 looking downstream. Outer electrode (23) is located coaxially within tube (18) by resilient fit with rings (25) (shown) and (26) (not shown). The inner rod electrode (24) extends coaxially with the tube and outer electrode except for its support and power connection portion (24a) which bends to penetrate the tube wall.

Figure 7:
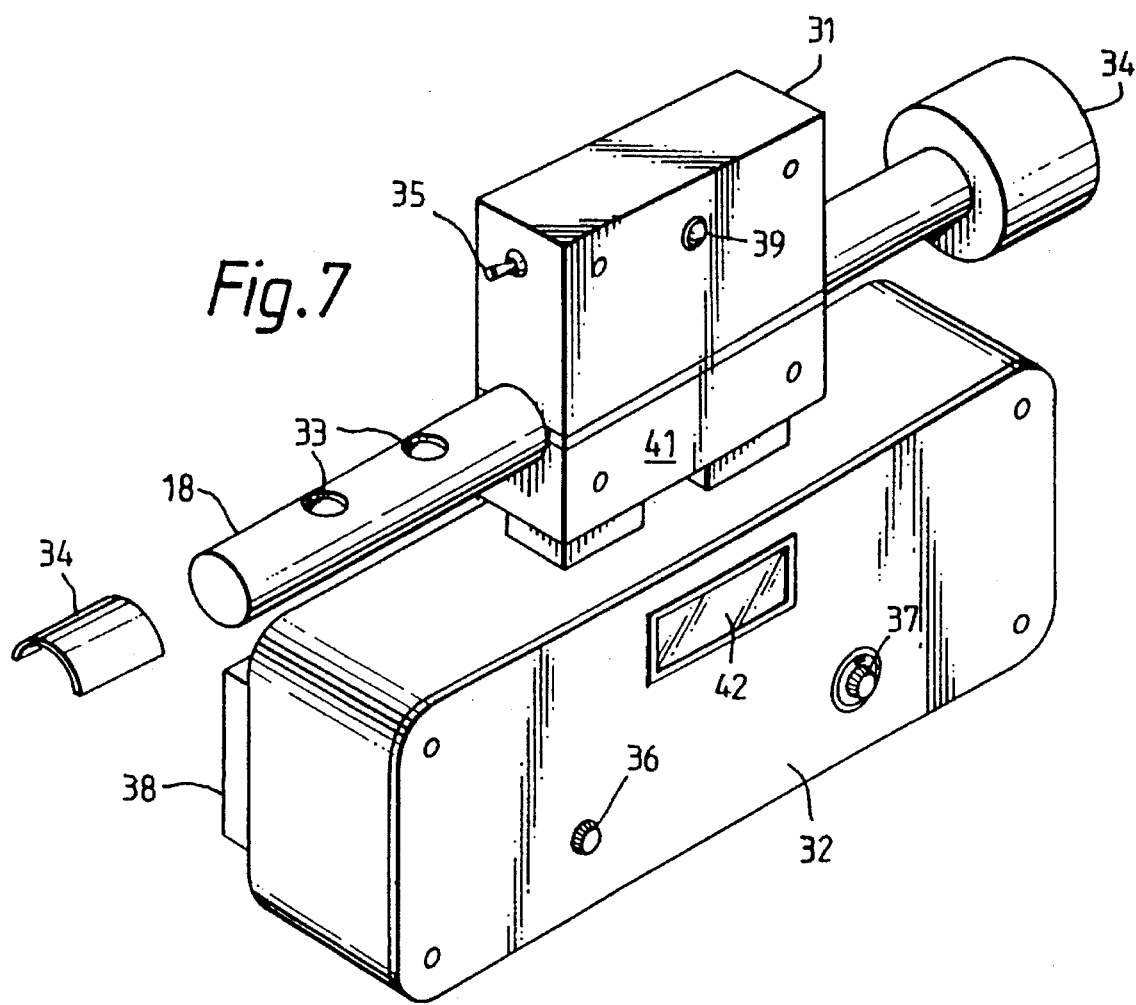
FIG. 7 shows a perspective view of the exterior of a device of the present invention having the configuration of FIG. 3 but with multiple apertures for varying the UV source to electrode distance.

The exterior of a complete device of the present invention is illustrated in FIG. 7. The tube (18), of interior configuration substantially as illustratad in FIGS. 4 or 5, is mounted so as to be movable along its longitudinal axis with respect to its support (41) and the ultraviolet source box (31). The power supply battery and circuitry for the reduction of drift and noise and the measurement of current passing between the electrodes is contained within a housing (32) upon which the tube support is mounted or may be provided separately ie. externally of the device. The gas flow induction means, in this case a fan unit (34), is provided at the outlet of the tube and both it and the UV source are powered by a source or sources held within box (31) and/or (32). A carrying handle or strap may also be provided (not shown).

The tube is provided with three ultraviolet light access apertures (33) over which slide covers (34) are placed when the apertures are not in use. By uncovering a selected aperture and moving the tube in the longitudinal direction, backward or forward as required, the selected aperture may be aligned with the UV source and thus the distance between the exciter zone and the coaxial electrode may be varied. In other embodiments these apertures may be provided as a continuous aperture or may be covered by UV penetrable glass such as magnesium fluoride glass. Variance of this distance provides adaptability in circumstances where different pollutants or tracers are being monitored having different excitabilty durations after action of the ultraviolet light. Furthermore, by increasing the time between excitation and detection, measurement of high levels of tracer may be determined by reference to known standards where previously known devices are overloaded.

The device carries controls for activating the ultraviolet light (35), for varying the sensitivity of the current sensing part of the circuitry (36), for backing off the zero reading (37) and for activating the electrode voltage (38). A visual indicator for indicating function of the light (39) and a visual current display (42) are provided.

Using a preferred configuration of the invention using the coaxial electrode arrangement of FIGS. 4, 5 and 6, with gold plated brass electrodes of about 4.5 cm length having a radial spacing of about 0.4 to 1 cm and with 300 to 1,000 volts across them, currents of the order of 10 nano-amps will be provided by near maximal ionised tracer levels contacting the electrodes: thus the current sensor will need to be sensitive to eg. from 100 pico-amps to 30–100 nano-amps.

Figure 8:
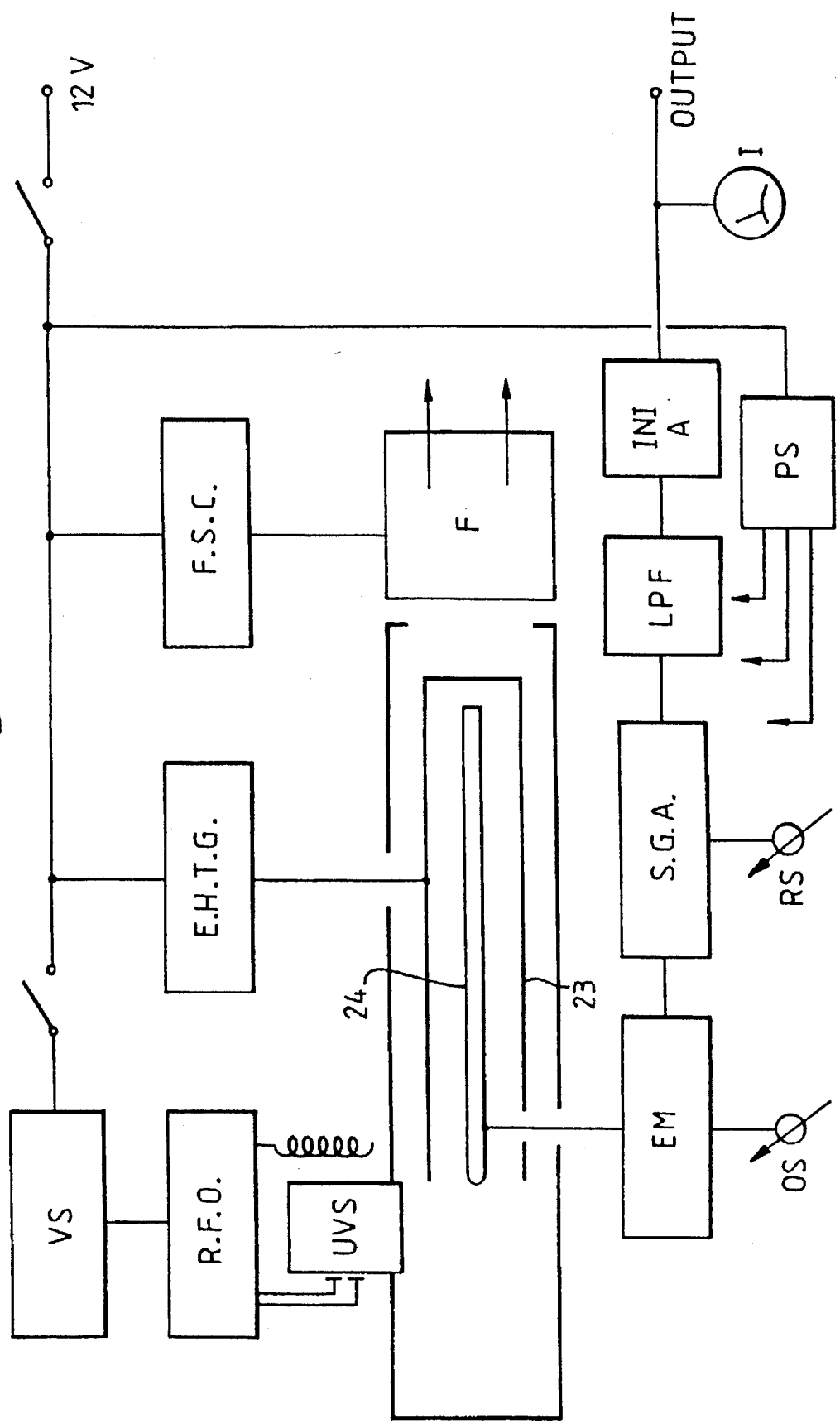
FIG. 8 shows a block diagram for a suitable electrical circuit for the device of the present invention.

FIG. 8 shows a block diagram for a circuit suitable for control of the devices of the present invention. The connections from EHTG to outer electrode 23 may instead be made to electrode 24 and vice versa and sensitive operation still applied. The features of the circuit are as follows: VS: voltage stabiliser, RFO; Radio frequency oscillator (or a DC-EHT unit in DC powered lamp devices). UVS; UV source, EHTG: 300 volts EHT generator, FSC: ran speed control, electrometer, SGA: switched gain amplifier, LPF: Low pass filter, INI A: Inv/Non-Inv amplifier, OS: off-set, RS: range switch, PS: power switch, I: ammeter and 12 V: 12 volts power supply (DC).

Figure 9:
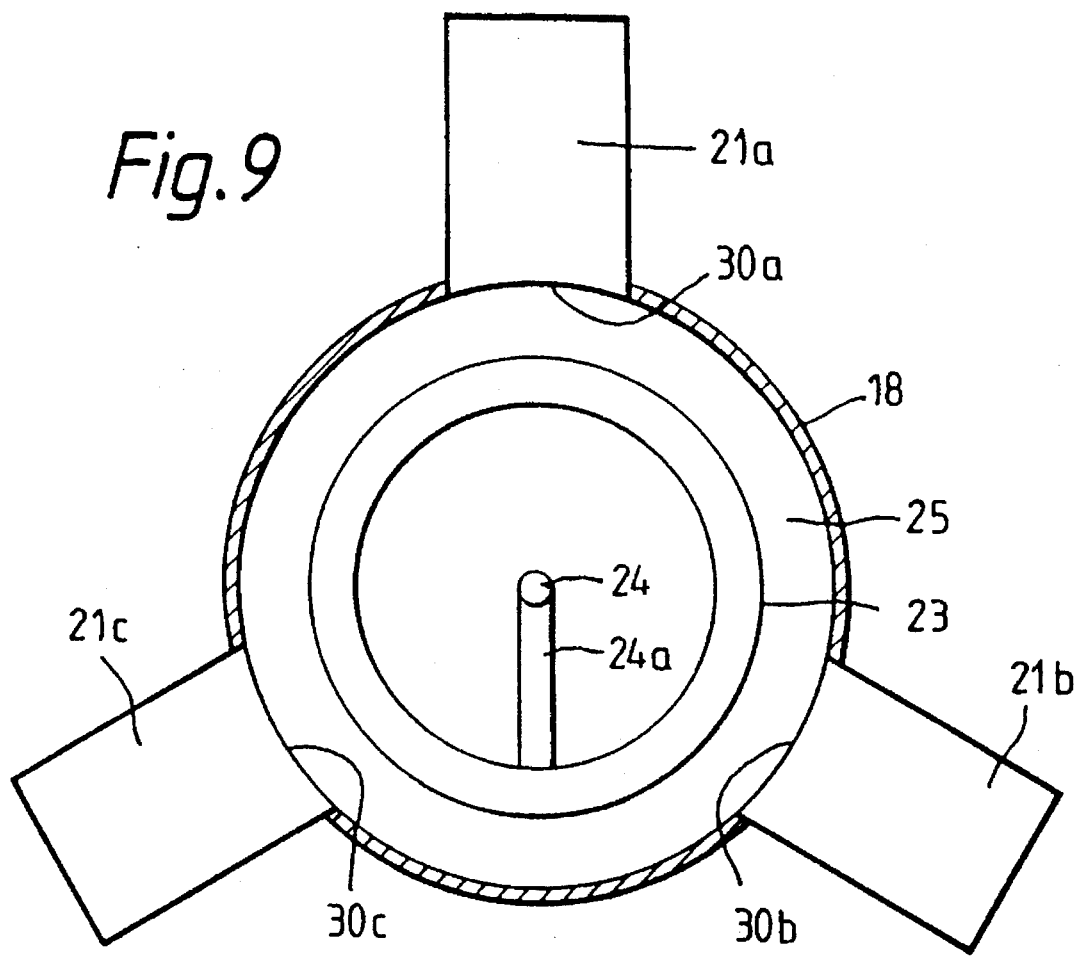
FIG. 9 shows a cross section of the irradiation zone of a conduit of a device of the invention, viewed from the inlet end, wherein three UV lamps provide the UV source.

FIG. 9 shows a cross section of the irradiation zone of a three UV lamp device of the invention viewed from the inlet wherein lamps (21a, 21b, 21c) irradiate the zone immediately upstream before electrode unit (23, 24, 24a, 25 having the same significance as those in FIG. 6). These lamps may emit the same or different UV wavelength (see description) dependent on application and may be independently energised.

Figure 10A:
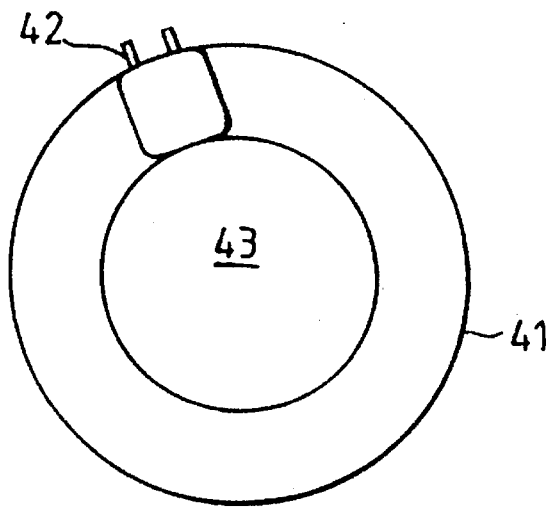
FIGS. 10a and 10b show an annular UV lamp arrangement for use with a further embodiment of the invention in end on and side views, 10a and 10b, respectively.
Figure 10B:
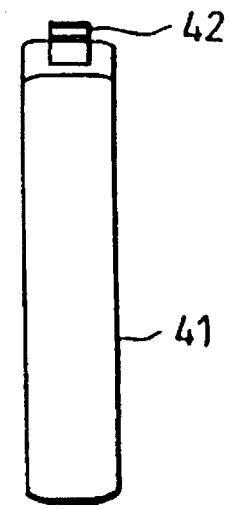

FIG. 10a and 10b show end on and side on views of the configuration of an annular UV light source that may be utilised to provide UV light from 360 degrees around a gas flow path in a device of the present invention. A UV light transmitting lamp enclosure (41) surrounds a space through which the gas flow path (43) extends and is energised by application of EHT, DC or AC, to connections (42).

I claim:

1. A method of quantification of an ultraviolet light ionizable gas or vapor in a gas sample at substantially atmospheric air pressure comprising the steps of:

(a) ionizing at least a part of any ultraviolet light ionizable gas or vapor present in the sample by irradiating said sample at substantially atmospheric pressure with a source of ultraviolet light;

(b) passing the irradiated sample through a gap between two electrode units having a voltage applied across them; and (c) measuring the current caused by ionized gas or vapor being neutralized by the electrode units and relating that to presence or amount of the ionizable gas or vapor;

wherein the ultraviolet light source is positioned relative to the electrode units such that ionization of the ionizable gas or vapor is substantially completed before the gas enters the gap between the electrode units and that at least a part of the irradiated gas or vapor passes through the gap to reach the outlet.

2. A device for the detection of ultraviolet light ionizable gas or vapor at substantially atmospheric pressure, said device comprising:

a conduit defining a gas flow passage having at least one inlet and at least one outlet;

an ultraviolet light source mounted for irradiating a portion of the passage and for at least partially ionizing said UV light ionizable gas vapor in said passage;

at least two electrodes mounted in a spaced fashion in the passage having coextensive portions facing each other;

a voltage supply circuit connected to the electrodes such that at least one electrode is differently charged with respect to one other electrode;

current measuring means sensitive to the effects of ions being neutralized upon the electrodes; and a gas flow induction means for drawings gas into said at least one inlet, through the irradiated portion of the passage at substantially atmospheric pressure, past the electrodes and out of said at least one outlet said at least two electrodes define a gap between differently charged electrode coextensive portions, said gap located substantially downstream of the irradiated portion of the passage such that at least part of the irradiated gas or vapor must pass through said gap to get to said one or more outlets, and the irradiation is not directed onto the electrodes from a downstream direction.

3. A hand holdable portable device for detecting ultraviolet (UV) light ionizable gas or vapor at substantially atmospheric pressure, said device including:

a conduit, said conduit defining a gas flow passage, said passage having at least one inlet, said inlet being adapted to have direct access to atmosphere, said passage also having at least one outlet, said outlet being adapted to exhaust directly to atmosphere;

an UV light source mounted such that in operation UV light traverses at least a portion of said passage at substantially right angles and so irradiates a portion of said passage and ionizes a portion of any UV light ionizable gas or vapor present in said passage;

an outer cylindrical electrode and an inner cylindrical electrode, said outer and inner electrodes being co-axially mounted in a spaced fashion in said passage downstream of said UV light source, said electrodes being positioned such that, in operation, UV light does not impinge thereon;

a voltage supply circuit connected to said electrodes such that at least one electrode is differently charged relative to the other;

current measuring means sensitive to the effects of ions being neutralized upon said electrode surfaces; and a gas flow induction means for drawing, at substantially atmospheric pressure, gas from atmosphere into said at least one inlet, through said irradiated portion of said passage, past said electrodes and out of said outlet to atmosphere.

4. A device as claimed in claim 3 having a substantially linear flow path through the entire device up to said flow induction means.

5. A device as claimed in claim 3 wherein co-extensive portions of said electrodes have a length in the direction of gas flow of at least that equal to their spacing.

6. A device as claimed in claim 3 wherein said passage diameter is from 1 to 5 cm.

7. A device as claimed in claim 3 wherein said UV irradiated portion of said passage is immediately upstream of said electrodes.

8. A device as claimed in claim 3 wherein an inner electrode or electrode unit is a single rod type electrode.

9. A device as claimed in claim 3 having an outer electrode with an inner diameter of from 0.6 cm to 4.5 cm.

10. A device as claimed in claim 3 wherein spacing between said inner diameter of said outer electrode and an outer diameter of said inner electrode is from 0.1 cm to 2.2 cm.

11. A device as claimed in claim 3 wherein said electrode units vary in diameter and form along their length.

12. A device as claimed in claim 3 wherein said UV light source is positioned outside said conduit and UV light enters through an aperture or UV transparent window.

13. A device as claimed in claim 3 wherein said UV source comprises more than one UV lamp.

14. A device as claimed in claim 3 wherein said UV source comprises an annular UV lamp capable of irradiating said conduit interior over angles of up to 360 degrees around said gas flow path.

15. A device as claimed in claim 13 wherein said UV source comprises lamps of different wavelength emission whereby UV light wavelength may be altered by an operator.

16. A method of quantification of an UV light ionizable gas or vapor in atmospheric air, said method comprising the steps of:

(a) positioning a hand holdable portable ionizable gas or vapor detector device in a position where it can intake from, and return to, atmosphere a sample of air at substantially atmospheric pressure, said device including:

a conduit, said conduit defining a gas flow passage, said passage having at least one inlet, said inlet being adapted to have direct access to atmosphere, said passage also having at least one output, said outlet being adapted to exhaust directly to atmosphere;

an UV light source mounted such that in operation UV light traverses at least a portion of said passage at substantially right angles and so irradiates at least a portion of said passage;

an outer cylindrical electrode and an inner cylindrical electrode, said outer and inner cylindrical electrodes being co-axially mounted in a spaced fashion in said passage downstream of said UV light source, said electrodes being positioned such that, in operation, UV light does not impinge thereon;

a voltage supply circuit connected to said electrodes such that at least one electrode is differently charged relative to the other;

current measuring means sensitive to the effects of ions being neutralized upon said electrode surfaces; and a gas flow induction means for drawing, at substantially atmospheric pressure, gas from atmosphere into said at least one inlet, through an irradiated portion of said passage, past said electrodes and out of said outlet to atmosphere;

(b) passing the air through said conduit at substantially atmospheric pressure and directing said beam of UV light at substantially right angles across said conduit to ionize at least a sample of any UV light ionizable gas or vapor present in said air;

(c) passing said ionized sample through a gap between said two spaced electrodes; and (d) measuring current caused by ionized gas or vapor being neutralized by said electrode units and relating said current to presence or amount of said ionizable gas or vapor.

17. A method as claimed in claim 16 wherein said gap between aid electrode units is defined by coextensive portions of said electrode units which extend for a length in the direction of gas flow.

18. A method as claimed in claim 16 wherein said UV irradiation is first carried out using one wavelength of UV light, then using a second wavelength of UV light, and a difference in current produced is used to determine one of the presence and quantity of a gas or vapor ionized by one of the wavelengths but not the other.

19. A method as claimed in claim 16 wherein said device is an environmental pollution monitoring device.

20. A device as claimed in claim 3 wherein said induction means samples gas at a rate of up to $4 \times 10^{-4}$ cubic meters $sec^{-1}$.

21. A device as claimed in claim 20 wherein said induction means samples gas at a rate of up to $4 \times 10^{-1}$ cubic meters $sec^{-1}$.

22. A method as claimed in claim 16 wherein said passing air step includes sampling gas at a rate of up to $4 \times 10^{-4}$ cubic meters $sec^{-1}$.

23. A method as claimed in claim 22 wherein said passing air step includes sampling gas at a rate of up to $4 \times 10^{-1}$ cubic meters $sec^{-}$.

* * * * *